United States Patent [19]
Pavelle et al.

[11] Patent Number: 5,228,573
[45] Date of Patent: Jul. 20, 1993

[54] PHARMACEUTICAL CAPSULE AND METHOD OF MAKING

[76] Inventors: Richard Pavelle, 23 Berkshire Dr.; Paul Burstein, 19 Glengarry; Ronald M. Latanision, 28 Nassau Dr., all of Winchester, Mass. 01890

[21] Appl. No.: 690,146

[22] Filed: Apr. 23, 1991

[51] Int. Cl.$^5$ .................. B65D 73/00; G01D 21/00; A61K 9/48
[52] U.S. Cl. .................. 206/459.1; 53/411; 53/454; 53/471; 53/472; 116/206; 424/454; 425/804
[58] Field of Search ............ 206/459.1, 807; 215/230; 116/206; 220/DIG. 34; 424/454, 451; 425/804; 53/411, 454, 471, 472

[56] References Cited

U.S. PATENT DOCUMENTS

| | | | |
|---|---|---|---|
| 3,463,532 | 8/1969 | Chidley et al. | 116/206 X |
| 3,899,295 | 8/1975 | Halpern | 206/459.1 |
| 4,098,577 | 7/1978 | Halpern | 206/459.1 X |
| 4,408,557 | 10/1983 | Bradley et al. | 116/206 |
| 4,505,399 | 3/1985 | Weiner | 215/230 |
| 4,511,052 | 4/1985 | Klein et al. | 215/230 |
| 4,526,752 | 7/1985 | Perlman et al. | 206/459.1 X |
| 4,813,541 | 3/1989 | Velasco et al. | 206/459.1 |
| 4,883,182 | 11/1989 | Hughes | 206/807 X |
| 4,890,763 | 1/1990 | Cunel | 206/459.1 X |

Primary Examiner—Bryon P. Gehman
Attorney, Agent, or Firm—Sprung Horn Kramer & Woods

[57] ABSTRACT

A method of packaging, comprising the steps of disposing an article in a package and airtightly sealing an air sensitive reagent, which changes color upon contact with air, as at least part of the package for the article such that the seal must be broken to access the article and thereby cause the reagent to contact the air or another agent and change color. A semi-permeable membrane will allow the same reagent to function as a shelf-life indicator.

6 Claims, 1 Drawing Sheet

PHARMACEUTICAL CAPSULE AND METHOD OF MAKING

BACKGROUND OF THE INVENTION

The present invention relates to methods and apparatus for alerting the consumer to tampering or unintentional violation of the integrity of packaging of any consumable product. Current packaging techniques use foils, blister packages, and heat seals, (among others) that present clear visual evidence of only the grossest of violations. In particular, an astute, sophisticated and malevolent intruder/terrorist can overcome current packaging technology quite easily to poison or otherwise tamper with the product in a way that is extremely difficult for a consumer to detect. The literature abounds with references to such behavior.

In a related area, manufacturers of time-sensitive materials, e.g., drugs and foods, have specific recommendations for the maximum effective shelf-life of any specific product. Very little technology has been applied to warning the consumer of the deterioration of these products, other than a date stamp. Indeed, under conditions of high temperature or photoactivated reactions, the deterioration will usually proceed at a faster rate than that envisioned by the manufacturer.

It is the intent of this invention to address dot of these areas simultaneously.

SUMMARY OF THE INVENTION

To this point, those knowledgeable in the field have not attempted to address these issues in a way that produces an unmistakable indicator to consumers. To this end, we will introduce the following concept: The Air Sensitive Reagent (ASR). We define the ASR to be a material that changes at least one of its physical characteristics when exposed to air or one of its constituent gases or components (e.g., water vapor or pollutants). The tampering indicator part of the invention depends on the reaction of an appropriate ASR with air that has penetrated an otherwise impermeable package. Any product that has been enveloped by an impermeable package has no physical contact with the external environment. Any attempt to physically reach the product will result in a penetration of the package, and external air will then enter the package. The ASR reacts to this external air, and undergoes physical change, for sake of illustration, a color change, which would be unmistakable by a normally sighted consumer. The only method for overcoming this ASR technique involves either destruction of the packaging material and a facsimile repackaging, or sophisticated vacuum techniques whose purpose is to exclude any external air.

The related invention of the visual indicator of expiration of time-sensitive material depends on the gradual interaction of an ASR (or other controlled reagent, as explained below). Essentially, the ASR changes color as air diffuses through a semi-permeable membrane.

Another implementation of the same packaging topography principle uses a laminate sheet material that totally envelopes the product. Two reactants, not necessarily parties to an air sensitive reaction, that change color are separated by a semi-porous interlayer. Any penetration of the package results in broaching the boundary between the two reactants, and a color change is initiated. The semi-porous boundary can be constructed to provide a time-sensitive indicator for the reactants to change color and thus provide a status of shelf-life or other lifetime.

The methods and apparatus described herein are primarily chemical and physical in nature. The main aim of these methods is providing color change a the most striking indicator of package penetration. Other methods of achieving penetration indicators are also discussed, but these are not as effective.

These and other objects and advantages are achieved in accordance with the present invention comprising a package and method of packaging comprising disposing an article in a package and airtightly sealing an air sensitive reagent, which changes color upon contact with air, as at least part of the package for the article such that the seal must be broken to access the article and thereby cause the reagent to contact the air and change color. The article is preferably one that is to be ingested or consumed, such as a drug, foodstuff or the like. The package can comprise an airtightly sealed capsule with the reagent disposed therein or a two layer blister package with the reagent disposed between the layers. The reagent is a manganese salt, other transition metal salts or other suitable inorganic compounds, an organic dye or other suitable organic compounds.

In another embodiment, first and second indicating substances are provided having respective first and second colors and reactible when in contact with each other to produce a third color which is different from the first and second colors. The first and second substances are sealed from each other as at least part of the package for the article such that the seal must be broken to access the article and thereby cause the first and second substances to contact each other and change color. The package preferably comprises a three layer blister package with the first and second substances disposed between the layers.

In a further embodiment, the first and second indicating substances are semi-porously sealed from each other as at least part of the package for the article such that the first and second substances contact each other over time and change color, whereby the color change indicates lack of freshness. The package preferably comprises a three layer blister package with the first and second substances disposed between the layers and the center layer comprising porous material.

In a still further embodiment, the air sensitive reagent, which changes color upon contact with air, is semi-porously sealed a at least part of the package for the article such that air contacts the reagent over time and the reagent changes color, whereby the color change indicates lack of freshness or other such shelf-life expiration.

BRIEF DESCRIPTION OF THE INVENTION

DETAILED DESCRIPTION OF THE INVENTION

The method presented here relies on one hundred percent coverage of a produce by an envelope. This envelope is effectively impenetrable by gases, and tough relative to normal handling loads, abrasions, and the like. Any attempt to tamper with the product must involve a penetration of the envelope. The penetration must result in a physical hole in the envelope through which air will be diffused. If an ASR is present within the envelope, then this air diffusion will change the color of the ASR to the warning indicator status. For example, manganous salts such as $MnSO_4$, $MnCl_2$, $Mn(NO_3)_2$ and $Mn(OH)_2$ are usable as an ASR in that they change color when exposed to air or air and water. Other transition metal salts or suitable inorganic compounds can be used. In the case of certain of these reactions, the color is determined by the relative amounts of oxygen and moisture made available and the reaction rates. Thus the pale pink manganous ion in the form of $MnSO_4$, for example, will react with air to produce the brown-black oxide $Mn_2O_3$.

One of the added benefits of these manganous reactions is that two technical issues are dispatched. The first is the safety of the ASR if consumed. These particular manganous compounds are non-toxic. The second issue is that any migration of the indicator agent into the product not affect the performance of the product Since these manganous compounds are insoluble, they will probably not affect the performance of the product, e.g., a pharmaceutical. Other ASR's besides inorganic salts, e.g. organic compounds, can provide similar color indicators as long as the aforementioned criteria are met. An example of a non-toxic organic compound that changes color upon air contact is the reduced form of the natural dye indigo. This is a colorless dihydro or leuco derivative which is oxidized to the deep blue indigo color when exposed to air. Other organic dyes or suitable organic compounds can be used.

Similarly, synthetic indigo (blue) can be produced by the exposure of indoxyl (yellow) to air.

Figure 1:
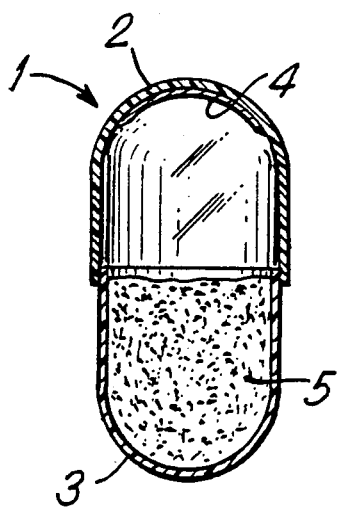
FIG. 1 is a sectional view of one embodiment according to the present invention.

The ASR can be packaged inside an impenetrable envelope as a dust, a gas, a suspension, or in any of many other forms. As shown in FIG. 1 a capsule 1 having a medication therein in powder form has two sealed halves 2,3 surrounding the medication. The half 2 is transparent and has a coating 4 of a ASR. The capsule is filled and sealed with no oxygen therein (assuming that the ASR is oxygen sensitive). If the capsule is tampered with, i.e. opened and refilled, the contact of the air with coating 4 will effect a color change.

Figure 2:
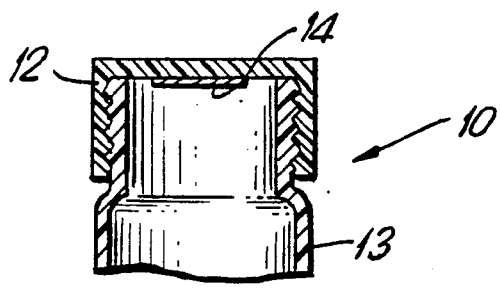
FIG. 2 is a sectional view of a second embodiment according to the present invention.

In FIG. 2 a unit 10 has a transparent cap 12 closing bottle 13. The cap has a layer 14 of an ASR. If the cap is opened prior to purchase, the color change will indicate this.

Figure 3:
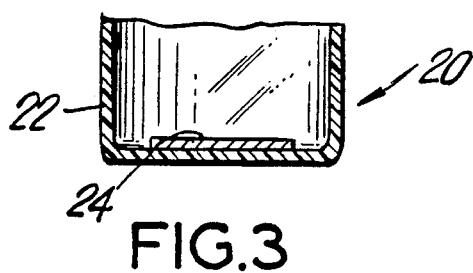
FIG. 3 is a sectional view of a third embodiment according to the present invention.

In FIG. 3, a transparent bottle 20 having such an indicator 24 at the bottom 22 would show at a glance by color whether the package had been exposed to air. The ASR can also be impregnated into a carrier material, which is itself used as a normal packaging component, for example, cotton or paper. For purposes of contamination detection, the only requirement is that the undisturbed package not have its ASR be exposed to air.

For purposes of time dating, the ASR is typically packaged inside a semi-permeable envelope where the reaction rate is a function of both the time required for air to permeate the envelope and the volume of air that has penetrated the package. Such an ASR may also be a function of the integrated temperature and humidity history of the package.

The type of ASR dictates the way in which the packaging process must be accomplished. If the ASR reacts to only very large quantities (large compared with the quantity of air included in the sealed package) of air over time, then the ASR can be packaged with the product in a relatively conventional way, care being taken to prevent the ASR from pre-reacting. If the ASR reacts to small quantities of air (comparable to the quantity of air contained within the package), then either an air absorber must be used or exclusion of the reacting component from air must be made.

Figure 4:
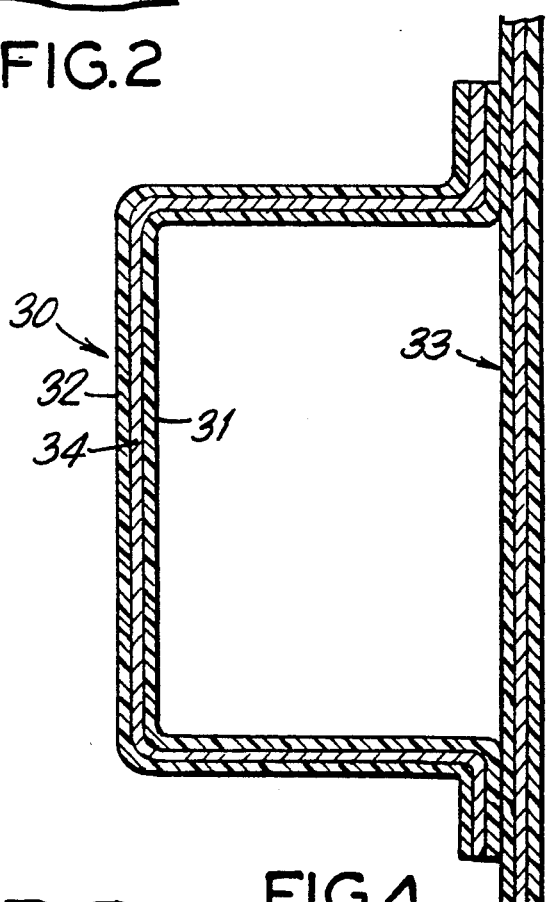
FIG. 4 is a sectional view of a fourth embodiment according to the present invention.

Another method of accomplishing the inclusion of the ASR is in the packaging material itself. For instance, a sandwich laminate 30 shown in FIG. 4 can be used as a packaging material, much as cellophane, polypropylene, or similar plastic materials are used. The outer sheets of the laminate 31,32 are a tough, non-porous material, while the middle section 34 contains the ASR. After the product is wrapped and sealed to a similarly constructed backing 33, any protrusion into the product will make a hole into the ASR layer. The result will be a color change in the region around the hole, where air infiltration was allowed. The advantage of such an approach is in the use of the sandwich laminate material in precisely the same way that current plastics are used to "seal" pharmaceuticals or other consumables.

Figure 5:
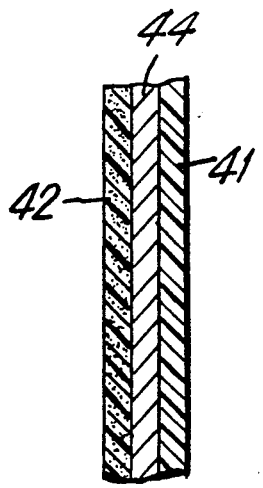
FIG. 5 is a sectional view of a fifth embodiment according to the present invention.

Another function is provided by a two layer sandwich shown in FIG. 5 with a well-defined semi-porous outer layer 42, interior to which is the ASR layer 44. The outer layer is a long time-constant porosity material (at least from the perspective of the ASR reactant) and the inner layer 41 is non porous. In this manner, after penetration through the layers to reach the product, the ASR layer will react in the normal way. However, the ASR will also change color of its own accord due to the long time-constant porous layer, which gradually leaks reactant through to the ASR. If this time-constant is chosen correctly (primarily through construction and thickness), then the ASR can be timed to react on a scale identical to the shelf-life of the product. Thus, the packaging itself will indicate that the product is no longer fit for use. If the reaction rates are chosen correctly, and the availability of the reactants is sufficiently well regulated, a number of different colors could result, where the resulting color is an indicator of shelf aging or penetration of the package. The only drawback with this scheme is that the toughness and resistance to accidental abrasion is probably not as high as a tough, impenetrable layer.

Figure 6:
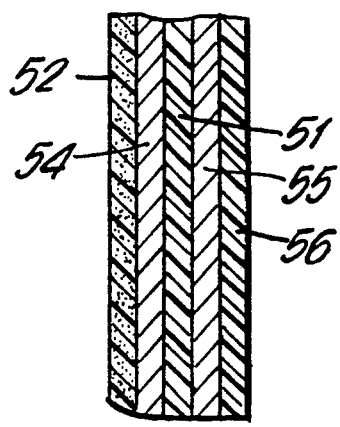
FIG. 6 is a sectional view of a sixth embodiment according to the present invention.

Another method of accomplishing a similar purpose is provided by a five layer sandwich shown in FIG. 6. In one embodiment, the outer laminates 51, 52 and 54 are identical to the outer layers 41, 42 and 44 in the laminate package of FIG. 5. The ASR is contained in the layer 54 just below the outside layer. The outer layer 52 contains the long time-constant layer. The fourth layer 55 contains a constituent for reaction with the ASR and layer 56, like layer 51 is a barrier layer. Penetration through the package results in the ASR's changing color. However, the five layer sandwich also has the ability to use a reaction that is not air induced, but could be temporal in nature. Specifically, the second and fourth layers can contain any set of desired reactants, not simply air induced reactions. If the third layer is semi-porous with an appropriate time constant for diffusion, then this can be used as a shelf-life indicator. Using non-air induced reactions simplifies manufacturing and packaging.

An example of such a five layer packaging scheme involves using phenolphthalein in citric acid in the fourth layer and milk of magnesia in the second layer. Migration across the semi-permeable layer will cause the phenolphthalein to change color.

A more mechanical packaging scheme utilizes the effects of back reflection of interference of visible light. For example, liquid crystal arrays can be used as the packaging material. This presents little problem in handling and packaging of the product. If any penetration of the package occurs, the appearance of the reflectivity at the point of penetration will be grossly changed. However, unless the penetration occurs over a very large region, these indicators may not be as readily observable to the casual consumer.

Much of the effort of economical use of this system relies on the method of packaging, on how different the packaging requirements are from present practice. In particular, any sealing in non-air environments may require significant expense. Air-cannibalizing reactions may be included at the time of packaging to obviate the necessity for accomplishing the packaging in a non-reacting atmosphere. There are many other approaches to this problem, which include, for example, vacuum application and backfilling with the reactant. This could be accomplished with a balloon-like package having a small nipple to evacuate the container before introducing the ASR, and finally sealing the package.

A generalization of this invention is also of use in the detection of tampered or spoiled food products. For instance, in the case of botulism, a reactant indicator (not necessarily an ASR) could be included inside the top of the can, where the consumer can see the indicator clearly. The color would be the indicator of the presence of the gas products of botulism.

What is claimed is:

1. A method of packaging, comprising the steps of:
   providing an ingestible capsule having a transparent portion and receptive of a pharmaceutical;
   coating an inner surface of the capsule at the transparent portion with a non-toxic ingestible air-sensitive reagent which is non-reactive with the pharmaceutical and which changes color upon contact with air; and
   air-tightly sealing the capsule with air removed and the pharmaceutical therein such that the seal must be broken to access the pharmaceutical and thereby cause the reagent to change color so as to be visible through the transparent portion.

2. The method according to claim 1, wherein the reagent is an inorganic compound.

3. The method according to claim 1, wherein he reagent is an organic compound.

4. A pharmaceutical package comprising:
   an ingestible capsule having a transparent portion and receptive of a pharmaceutical;
   a coating on an inner surface of the capsule composed of a non-toxic ingestible air-sensitive reagent which is non-reactive with the pharmaceutical and which changes color upon contact with air; and
   means air-tightly sealing the capsule with air removed and the pharmaceutical therein such that the seal must be broken to access the pharmaceutical thereby causing the reagent to change color so as to be visible through the transparent portion.

5. The package according to claim 4, wherein the reagent is an inorganic compound.

6. The package according to claim 4, wherein the reagent is an organic compound.

* * * * *